United States Patent [19]

Eickmann

[11] Patent Number: 4,882,029
[45] Date of Patent: Nov. 21, 1989

[54] ELECTRODE SYSTEM

[75] Inventor: Guenter Eickmann, Grove City, Pa.

[73] Assignee: Pine Instrument Company, Grove City, Pa.

[21] Appl. No.: 12,884

[22] Filed: Feb. 10, 1987

[51] Int. Cl.$^4$ ............................................. G01N 27/46
[52] U.S. Cl. .................................. 204/400; 204/286; 204/297 R; 204/416; 204/435
[58] Field of Search ............... 204/400, 416, 418, 419, 204/435, 286, 297 R

[56] References Cited

U.S. PATENT DOCUMENTS

| | | | |
|---|---|---|---|
| 3,492,216 | 1/1970 | Riseman et al. | 204/435 |
| 3,793,176 | 2/1974 | Jerrold-Jones | 204/435 |
| 3,882,011 | 5/1975 | Hines et al. | 204/195 |
| 4,314,896 | 2/1982 | Binder et al. | 204/195 |
| 4,502,214 | 3/1985 | Miles et al. | 204/435 |
| 4,592,825 | 6/1986 | Crevoiserat | 204/428 |
| 4,730,389 | 3/1988 | Baudino et al. | 204/428 |

OTHER PUBLICATIONS

ASR2 Rotator Data Sheet, 11/83.
Electrodes Data Sheet, 8/83.
Square-Wave Reprint ©1983.
RDE3 Operating Instruction, undated.

Primary Examiner—T. Tung
Attorney, Agent, or Firm—Calfee, Halter & Griswold

[57] ABSTRACT

An electrode, particularly a miniature electrode, having structural integrity and reliable electrical operation results. A thin fluoroplastic liner, preferably, a TFE fluorocarbon liner, seals an electrode disc core to a PCTFE fluoroplastic shroud. By properly machining and assembling the electrode disc core, TFE fluorocarbon liner and PCTFE fluoroplastic shroud, a fluid tight interference seal is obtained to avoid the electrolytic fluid leaking into the electrode to corrode the conductive electrical path. A stainless steel spring extends between the electrode disc core and an electrode contact in the PCTFE fluoroplastic shroud to complete the conductive path through the electrode. The spring has two flat ends which are held in reliable surface contact with the disc core and the electrode contact by the bias of the spring itself. The spring thus provides a reliable electric connection with good conductivity.

11 Claims, 2 Drawing Sheets

ELECTRODE SYSTEM

FIELD OF THE INVENTION

The present invention generally relates to an electrode for electrolytic fluid testing and specifically relates to a miniature electrode having an electrode disc core sealed to a PCTFE fluoroplastic shroud by a TFE fluorocarbon liner.

BACKGROUND OF THE INVENTION

Miniature electrodes for electrically sensing physical characteristics of electrolyte fluids are particularly useful for testing small fluid samples contained in small cells or beakers. A miniature electrode is defined in the industry as having an outside diameter of less than 12 millimeters, which is slightly less than one-half inch.

The conventional miniature electrode in the prior art has been formed from a hollow glass tube support with a glassy carbon disc fused over the lower end. A copper wire extends from the fused glassy carbon disc through the hollow glass tube to provide the electrical conductivity for the miniature probe. The glassy carbon disc and copper wire do not provide highly accurate current readings and thus the predictability and accuracy of the test results may be suspect. The glassy carbon electrode cannot be satisfactorily replaced by a more accurate noble metal electrode disc since a fluid tight seal with the glass tube is difficult, if not impossible, to obtain. Without a satisfactory seal, the highly corrosive electrolyte is free to seep into the glass tube and corrode the copper conductor to minimize or destroy the effectiveness of the miniature probe. Moreover, glass miniature probes are extremely fragile due to their glass construction and their small diameter relative to length. Therefore, the miniature glass electrodes are frequently broken requiring relatively expensive replacement.

The assignee of the present invention has sold a plastic electrode in several sizes, one of which approaches the outer diameter size of a miniature electrode. This plastic electrode included an electrode disc core comprising a noble metal electrode disc soldered to a stainless steel substrate. The substrate includes a smaller diameter disc projection and a larger diameter body section. The substrate body section had a threaded blind end bore adapted threadedly to receive part of the electrode arbor. The substrate and electrode disc were inserted into a TFE fluorocarbon sleeve having an outer diameter as small as 0.472 inches. The TFE fluorocarbon sleeve was shrunk fit into an interference fit with the stainless steel substrate to form a seal therebetween. While this electrode has successfully been used for several years, the TFE fluorocarbon sleeve may have oxygen bubbles captured therein or thereon which potentially might affect current readings when the TFE fluorocarbon sleeve is partially submerged in the electrolytic fluid.

SUMMARY OF THE INVENTION

The principle object of the present invention is to provide an electrode having structural integrity and improved electrical operational results. This principle object is accomplished by using a thin fluoroplastic liner to seal an electrode disc core to a different fluoroplastic shroud. Preferably, a TFE fluorocarbon liner seals an electrode disc core to a PCTFE fluoroplastic shroud. By properly machining and assembling the electrode disc core, TFE fluorocarbon liner and PCTFE fluoroplastic shroud, a fluid tight interference seal is obtained to avoid the electrolytic fluid leaking into the electrode to corrode the conductive electrical path.

It is another object of the present invention to provide a sealed electrode disc core in a miniature electrode probe having good electrical conductivity therethrough. To accomplish this object, a stainless steel spring extends between the electrode disc core and an electrode contact in the PCTFE fluoroplastic shroud to complete the conductive path through the electrode. The spring has two flat ends which are held in reliable surface contact with the disc core and the electrode contact by the bias of the spring itself. The spring thus provides a reliable electric connection with good conductivity.

It is yet another object of the present invention to provide a sealed electrode by assembly steps providing structural and operational integrity. By employing an electrode disc core, TFE fluorocarbon liner and PCTFE shroud, the parts can be accurately turned or machined for concentric, frictional, interference engagement to form a fluid tight seal. This seal between the electrode disc core and PCTFE shroud may be obtained by a thin TFE fluorocarbon liner being thermally contracted for sealing contact with the electrode disc core and subsequently being thermally expanded for sealing with the PCTFE shroud. The final assembled electrode has the structural strength required for normal laboratory handling and the operational advantages provided by having a well sealed electrode disc core conductively coupled to an electrode contact by a coiled spring.

It is still another object of the present invention to provide a miniature electrode probe tip with sealed electrode disc core that can readily be installed on or removed from an electrode arbor. For this purpose, a section of the PCTFE shroud bore may be threaded rotatably to receive a threaded nipple section of the arbor. This threaded connection allows the same arbor and test set up to be used with numerous probe tips having different electrode discs and sizes as required by the specific fluid being tested.

It is yet another object of the present invention to provide an electrode construction concepts which, although particularly useful for constructing a miniature electrode, are also useful for constructing electrodes other than of the miniature electrode type.

The invention, then, comprises the features hereinafter fully described and particularly pointed out in the claims, the following description and annexed drawings setting forth in detail certain illustrative embodiments of the invention, these being indicative, however, of but a few of the various ways in which the principles of the invention may be embodied.

DETAILED DESCRIPTION OF THE PREFERRED EMBODIMENTS

A. Exemplary Test Set Up Employing Miniature Electrode

Figure 1:
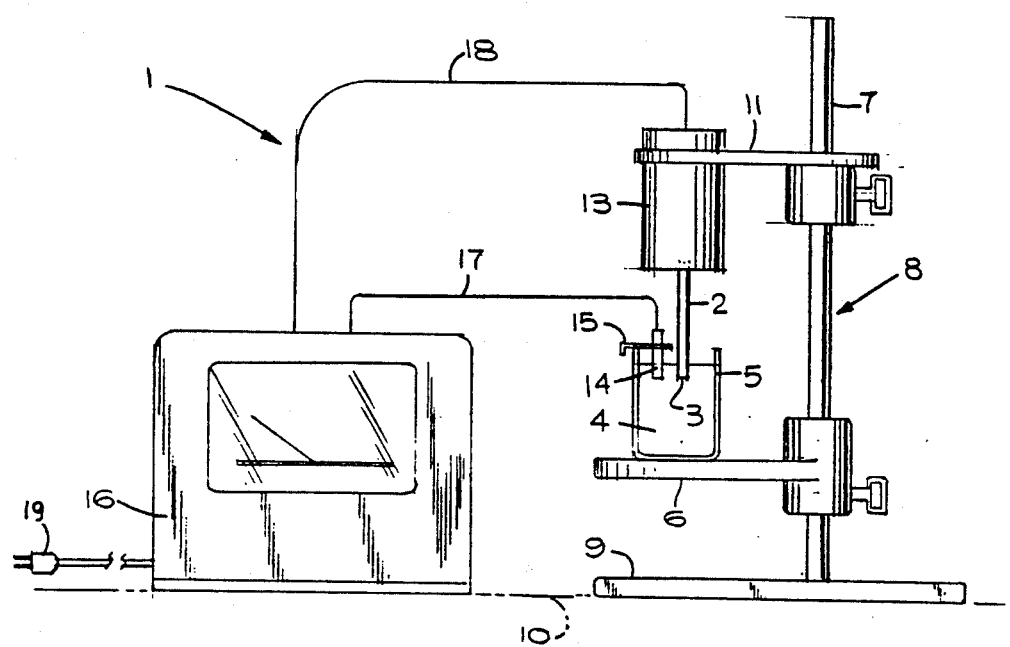
FIG. 1 is an elevation schematically illustrating a miniature electrode probe in an exemplary electrolytic circuit for fluid testing.

Turning now in more detail to the drawings and initially to FIG. 1, an electrolytic circuit for fluid testing is indicated generally at 1. The electrolytic circuit includes a miniature probe 2 having an electrode disc 3 at its lower end submerged in the electrolytic fluid 4 being tested. The electrolytic fluid 4 is contained in a cell or beaker 5 and has any dissolved oxygen therein removed by nitrogen saturation or purging. The beaker 5 is supported on a vertically adjustable platform 6 cantilevered from vertical column 7 of support stand 8. The vertical column 7 is mounted on base 9 resting on a lab bench 10.

A support bracket 11 is also vertically adjustable along and cantilevered from column 7. The bracket 11 supports a probe mount 13 releasably holding the miniature probe 2. As shown, the miniature pobe depends vertically downwardly from the mount 13 but may be inclined and/or rotated if required by the test set up or by the fluid being tested. The bracket 11 and/or platform 6 can be selectively vertically adjusted along column 7 in accordance with the size of the probe and beaker to submerge the electrode disc 2 in the electrolytic fluid 4 as illustrated.

A reference saturated calomel electrode 14 is also partially submerged in electrolytic fluid 4. The reference probe 14 is suitably mounted by a clamp 15 or the like to beaker 5 or to any other support. The reference probe 14 is connected to potentiostat 16 by electrical lead 17. The potentiostat 16 is also electrically connected to miniature probe 2 by electrical lead 18 and probe mount 11. The potentiostat 16 can be connected by plug 19 to a suitable source of power to energize circuit 1. The exemplary circuit 1 thus includes potentiostat 16, lead 18, probe mount 13, miniature probe 2, electrolytic fluid 4, reference probe 14 and lead 17 back to potentiostat 16.

The application of voltage to circuit 1 allows the current through the circuit to be measured, displayed and/or recorded by potentiostat 16. Potentiostats for this purpose are available, for example, from EG&G, Hewlett Packard and the assignee of the present invention. The electrical current measured through circuit 1 is indicative of the potential of the electrolytic fluid 4, which allows the characteristics of that fluid to be determined by computer or manual comparison to known standards. The use of the miniature probe of the present invention in the exemplary circuit provides increased reliability and improved operational results.

B. The Electrodes of Present Invention

An electrode according to the present invention includes an electrode disc core sealed to a fluoroplastic shroud by a different fluoroplastic liner. The preferred mode of practicing the invention is using a PCTFE fluoroplastic shroud with a thin TFE fluorocarbon plastic liner to obtain a thermally effected interference seal between the electrode disc core and PCTFE fluoroplastic shroud. The PCTFE fluoroplastic shroud has a first bore portion receiving the TFE fluorocarbon and electrode disc core subassembly and a second bore portion receiving an electrode contact. A coil spring extends between the electrode disc core and the electrode contact to complete the conductive path through the electrode. In this application, reference to an electrode disc core is intended to mean a conductive member having an electrode disc portion intended to directly contact an an electrolytic fluid. The electrode disc core preferably includes a metal disc electrode (formed e.g. of a noble metal) or a glassy carbon electrode. A detailed description of the preferred embodiments of this invention is set forth below.

1. Miniature Electrode of FIG. 2

Figure 2:
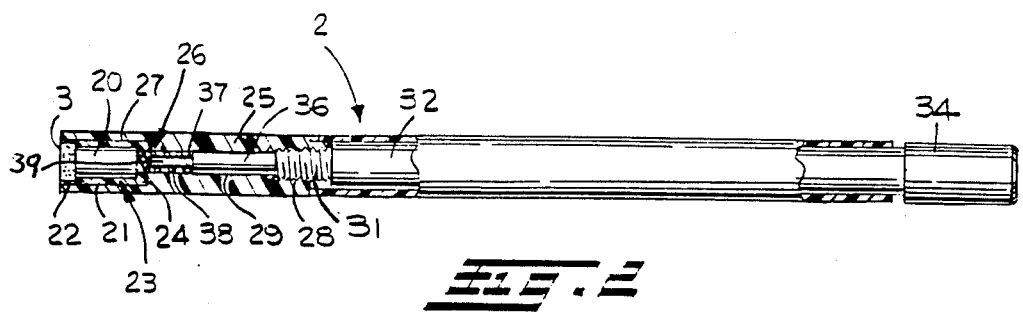
FIG. 2 is a cross section of a miniature probe according to one embodiment of the invention.

Referring to FIG. 2, miniature probe 2 includes a noble metal electrode disc 3. The noble metal electrode disc 3 is preferrably made of gold, silver or platinum. The noble metal electrode disc 3 is conductively soldered, such as by silver solder, to a conductive metal core 20 to form an electrode disc core. The metal core 20 is preferably solid stainless steel. As shown, the electrode disc 3 has a larger outer diameter than the conductive metal core 20. The electrode disc core has its outer diameter accurately machined for concentricity to enhance the assembly process.

The electrode disc core is received in and sealed to a thin TFE fluorocarbon liner 21 which is of generally tubular shape. Preferably liner 21 is virgin polytetrafluoroethylene (PTFE) plastic. PTFE plastic is available from DuPont under the trademark Teflon and from Allied Corp. under the trademark Halon. The generally tubular TFE fluorocarbon liner 21 has an annular recess 22 at its forward inner end to receive tightly the larger diameter electrode disc 3. The TFE fluorocarbon liner 21 also has an axially inward portion 24 having a smaller inner diameter than the electrode disc core. The portion 24 of the TFE fluorocarbon liner defines a U-shaped base cup which is designed to seat between the electrode disc core and a supporting shroud (described hereinafter) during the assembly process.

The tubular TFE fluorocarbon liner 21 may have a wall thickness of approximately 0.023 inches at annular recess 22 and approximately 0.052 inches along the rest of its length up to the U-shape base cup 24. The inner diameter of the main body portion of tubular TFE fluorocarbon liner 21 is approximately 0.089 inches and the outer diameter of the TFE fluorocarbon liner is approximately 0.141 inches. The inner diameter of the TFE fluorocarbon liner and its annular recess is selected to provide at ambient temperatures an interference frictional fit with the outer diameter of the electrode disc core. In other words, the outer diameter of the electrode disc core is slightly greater than the inner diameter of the TFE fluorocarbon liner at ambient temperatures. In the example given, the outer diameter of the metal core 20 could be 0.0960 inches compared to the 0.0890 inch inner diameter of the TFE fluorocarbon liner at ambient temperatures. The inner diameter of the TFE fluorocarbon liner 21 and recess 22 are accurately turned or finished for concentricity with the outer diameter of the electrode disc core.

To assemble the electrode disc core in the TFE fluorocarbon liner, the TFC fluorocarbon liner and base cup are heated to approximately 350° F. for approximately one-half hour or more. Because of its material characteristics, including its coefficient of thermal expansion, the heated TFE fluorocarbon liner 21 and U-shaped base cup 24 uniformly radially expand. The temperature and heating time are selected to allow the TFE fluorocarbon liner radially to expand sufficiently that the inner diameter of the liner is approximately equal to the outer diameter of the electrode disc core. The ambient temperature electrode disc core is then inserted into the heated and radially expanded TFE fluorocarbon liner 21 and U-shaped base cup in a frictional push fit. The electrode disc core is axially coextensive with the TFE fluorocarbon liner and is accurately positioned therewithin during insertion by the electrode disc 3 engaging annular recess 22 of TFE fluorocarbon liner 21 and the electrode disc core seating against the TFE fluorocarbon U-shaped base cup 24. The TFE fluorocarbon liner is then allowed to cool to ambient temperatures. Because of its elastic memory, the TFE fluorocarbon liner 21 radially contracts during the cooling process to provide a tight shrink fit on the disc core. Because of the accurately machined abutting surfaces and proper selection of the relative dimensions, the interference engagement provided by the shrink fit uniformly along the length of the abutting surfaces results in a fluid tight seal between the electrode disc core and TFE fluorocarbon liner.

The completed electrode disc core and liner assembly, indicated generally at 23, is then received in and sealed to the bore section of a fluoroplastic shroud 25. The shroud 25 may have an outer diameter of 0.200 inches in the example given. Preferably, the fluoroplastic shroud is made from a polychlorotrifluoroethylene (PCTFE) fluoroplastic material. The PCTFE fluoroplastic material is stronger and harder than the TFE fluorocarbon plastic material. PCTFE fluoroplastic is available from The Minnesota Mining and Manufacturing Company under the trademark KEL-F. The preferred PCTFE material is sold under the trademark KEL-F 81.

The PCTFE shroud 25 has a stepped bore, indicated generally at 26, extending therethrough. The stepped bore 26 includes an enlarged forward end section 27, a threaded rear end section 28 and a central reduced diameter section 29 interconnecting the front and rear sections. The front end section 27 of bore 26 in the PCTFE shroud 25 receives the electrode disc core and liner assembly 23.

The PCTFE material may be accurately turned or machined for precision assembly. The front end section 27 of bore 26 through shroud 25 is accurately surface finished to a concentric inner diameter dimensioned to provide a tight interference fit with the outer diameter of the TFE fluorocarbon liner seal. Specifically, the inner diameter of bore section 27 is less than the outer diameter of the TFE fluorocarbon liner 21 at ambient temperature. As an example, the inner diameter of front end section 27 of bore 26 may be approximately 0.1370 inches, which will provide a tight interference fit with the normal outside diameter of approximately 0.141 inches for the TFE fluorocarbon liner 21.

In assembling the electrode disc core and liner assembly 23 with the PCTFE shroud, the electrode disc core and liner assembly 23 is placed in a freezer having a temperature well below the freezing point, preferably between minus 15° F. and minus 20° F.. The electrode disc core and liner assembly 23 is left in the freezer for at least one-half hour. The exposure to freezing temperatures results in contraction of the TFE fluorocarbon liner and the U-shaped base cup 24. The temperature and freezing period are selected to obtain sufficient liner contraction to have the outer diameter of the liner be approximately equal to the inner diameter of bore section 27 when the PCTFE shroud is at ambient temperatures. After sufficient radial contraction has been obtained, the electrode disc core and liner assembly 23 is removed from the freezer and inserted in the front end section 27 of bore 26 of the room temperature PCTFE shroud.

The relative dimensions of the liner and shroud are selected in accordance with the thermal expansion and contraction characteristics of the liner to result in the disc core and liner assembly 23 having to be frictionally push fit into the shroud bore after removal from the freezer. The end of the liner 21 initially inserted into shroud 25 may be slightly inwardly tapered on its outer diameter or may have an annular radius or chamfer formed thereon initially to assist in pushing the disc core and liner assembly into the shroud. The length of the disc core and liner assembly 23 (including the U-shaped base cup 24) is coextensive with the length of bore section 27 resulting in the electrode disc 3 being flush with the front end of miniature probe 2 after insertion. The inserted TFE fluorocarbon liner material is then allowed to return to ambient room temperature. Due to its elastic memory, the TFE fluorocarbon liner 21 will begin radially to expand as its temperature increases in the ambient temperature environment. When the TFE fluorocarbon liner 21 has returned to ambient temperature, the radial expansion will have locked the disc core and liner assembly 23 in the front end section 27 of bore 26 in a fluid tight seal due to frictional interference therebetween along their entire axial lengths. The U-shaped TFE fluorocarbon base cup helps hold the liner in proper orientation during the assembly process.

The rear end section 28 of bore 29 in shroud 25 is provided with means to hold the electrode contact of the electrode. As shown, internal threads are provided in the rear end section 28 of bore 29. These internal threads selectively threadedly receive an externally threaded section 31 on the electrode contact, shown in the preferred mode as metallic electrode arbor 32. The arbor 32 is protectively covered with a tubular insulation sleeve 33, preferably made of TFE fluorocarbon material. The arbor 32 has a connection head 34 at its rear end which is coupled to mount 13 both mechanically and electrically.

As shown in FIG. 2, the arbor 32, which is preferrably made of stainless steel, has a shaft 36 extending forwardly from threaded section 31. The shaft 36 includes an integral reduced diameter portion 39 and a shoulder 37 is formed between the shaft 36 and the reduced diameter portion 39. A coil spring 38 is received in central bore section 29 of shroud 25. The distal end of the reduced diameter portion 39 is spaced from the conductive metal cove 20, and the spring 38 surrounds and is axially longer than the forward reduced diameter portion 39 of shaft 36. The forward reduced diameter portion 39 of shaft 36 guides the spring and provides additional surface contact with the spring to enhance conductivity therebetween.

The spring 38 is preferably stainless steel and has two flat coiled ends. The flat coiled ends respectively provide maximum surface contact with the core 20 and with the shoulder 37 of arbor 32. By having spring 38 slightly axially longer than the reduced diameter end of the stepped shaft 36, good surface contact between the core 20 and arbor shoulder 37 is assured when the shroud 25 is threaded onto the threaded section 31 of arbor 32. Moreover, the coil spring 38 is slightly compressed resulting in the ends thereof being positively held against the core 20 and arbor shoulder 37 by the spring bias to enhance the electrical conductivity therebetween.

The miniature probe of FIG. 2 has its electrical conductive path through electrode disc 3, metal core 20, stainless steel coil spring 38, and arbor 32. This conductive path is totally sealed from the electrolyte fluid by the TFE fluorocarbon liner 21 and by the PCTFE shroud 25. Because of the accurate concentricity of the finished parts, the materials used and the assembly process employed, a fluid tight interference seal is obtained to avoid electrolyte leakage and any resultant corrosion, while providing the enhanced conductivity and accuracy of an electrode disc in a miniature probe environment. By using a thin TFE fluorocarbon sealing liner, the good sealing characteristics of the TFE fluorocarbon material can be utilized and protected by a PCTFE shroud covering, while minimizing oxygen or trapped oxygen content by limiting the TFE fluorocarbon material used and by push fitting the parts into one another. The PCTFE shroud with the disc core assembled and sealed therein can be readily installed on and removed from the electrode arbor by the threaded connection provided. Therefore, a number of PCTFE shrouds may be provided with different metal discs and/or different dimensions as required by the application.

2. Miniature Electrode of FIG. 3

Figure 3:
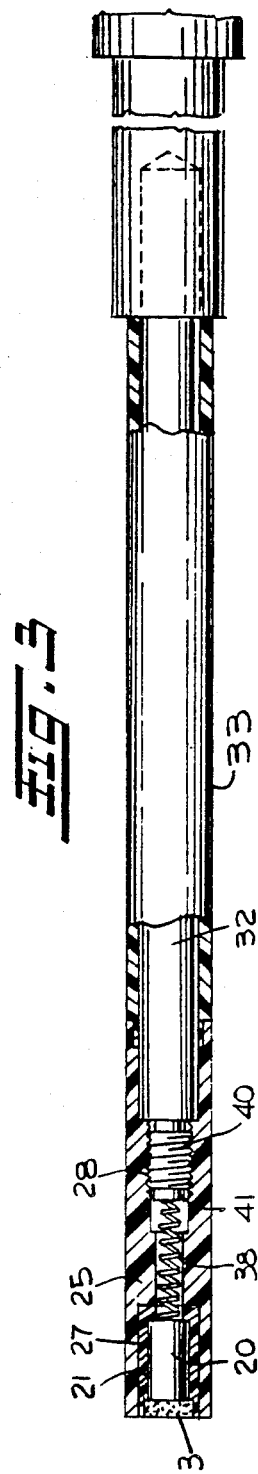
FIG. 3 is a cross section of the miniature probe according to another embodiment of the invention.

Turning now to FIG. 3, another embodiment for miniature probe 2 is illustrated. This embodiment is basically the same as the first embodiment with respect to the electrode disc 3, metal core 20, liner 21, shroud 25 and the method for assembling the same. However, the arbor 32 of the second embodiment is slightly different.

The forward end of arbor 32 terminates in a threaded nipple 40. The PCTFE shroud 25 is selectively mounted on the arbor 32 by screwing the threaded section 28 of the shroud bore onto the threaded nipple 40. A stainless steel anti-friction washer 41 may be positioned on the front end of nipple 40 on arbor 32. This anti-friction washer 41 permits the shroud 25 to be screwed onto the arbor with little, if any, of that rotation being imparted to the coil spring 38. The conductivity path through electrode 2 in FIG. 3 thus includes disc 3, core 20, spring 38, washer 41 and arbor 32.

It will be apparent from the foregoing that changes may be made in the details of construction and configuration without departing from the spirit of the invention as defined in the following claims. For example, while the preferred embodiment is for a mini-electrode (FIGS. 1-3), the electrode illustrated and described herein can be made in full size electrodes having outer diameters in excess of 12 millimeters or other fluoroplastic material combinations can be used to effect the fluid tight interference seals. Additionally, it will be clear to those of ordinary skill in the art that an electrode according to the invention can be supported for rotation in the electrolytic fluid, or the electrode can be supported in a fixed position, and the electrolytic fluid caused to flow past the electrode. Further, while the disclosed preferred embodiment relates to an electrode assembly in which the electrode, the electrode contact and the bores in the shroud are all coaxial, the principles of the invention can be used to form electrode assemblies in which the electrode and the electrode contact are disposed in bores that extend at angles relative to each other.

I claim:

1. An electrode for electrically sensing characteristics of electrolytic fluids being tested comprising an electrode disc core, a TFE fluorocarbon plastic liner receiving the electrode disc core assembled therein and sealed thereto, a PCTFE plastic shroud having a first bore portion, said first portion having the assembled electrode disc core and liner received and sealed therein, the PCTFE plastic shroud having a second bore portion receiving at least part of an electrode contact, and a spring extending in the second bore portion between the electrode contact and the electrode disc core to complete the conductive path from the disc selectively submerged in the fluid.

2. The electrode of claim 1 wherein the spring is stainless steel and has two planar ends for respective maximum surface contact with the electrode disc core and electrode contact.

3. The electrode of claim 1 wherein the shroud is a longitudinally extending member with a longitudinal bore extending therethrough, said bore being stepped to define two larger cylindrical end sections and a smaller cylindrical central section interconnecting the end sections, one of said larger cylindrical sections defining said first bore portion, the other of said larger cylindrical end sections and said smaller cylindrical central section defining said second bore portion, said other of said larger cylindrical end sections threadedly receiving the electrode contact and said spring being disposed in said smaller cylindrical central section.

4. The electrode of claim 1 wherein the electrode disc core is surface finished for concentricity and includes a noble metal electrode disc conductively soldered to a solid steel cylindrical core.

5. The electrode of claim 4 wherein the electrode disc core is frictionally sealed within the TFE fluorocarbon liner, said liner being accurately sized on its inner diameter normally to be slightly smaller than the outside diameter of the disc core for a tight frictional interference fit therebetween when assembled.

6. The electrode of claim 5 wherein the electrode disc has a slightly larger diameter than the core and the inside diameter of the liner has an annular recess therein tightly receiving the electrode disc.

7. The electrode of claim 1 or claim 3 wherein the electrode contact comprises an arbor having a threaded nipple section thereon threadedly mating with threads on the inside diameter of the second bore portion of the shroud.

8. The electrode of claim 7 further comprising an antifriction washer on the leading edge of the nipple section in conductive engagement with the spring and to permit the arbor to rotate for threading without rotating the spring.

9. The electrode of claim 7 wherein a stepped shaft on the arbor extends forwardly from the nipple section to define a shoulder for conductively seating one end of the spring and further to define a guide received within the spring for stability and increased surface contact.

10. The electrode of claim 9 wherein the maximum outside diameter of the PCTFE shroud is approximately 12 millimeters.

11. An electrode for electrolytic fluid testing comprising an electrode disc core, an electrode contact, a spring electrically connecting the electrode disc core to the electrode contact, a PTFE flurocarbon plastic shroud encasing the electrode disc core, spring and at least part of the electrode contact and a TFE fluorocarbon plastic liner sealing the disc core to the shroud.

* * * * *